(12) United States Patent
Dwyer (10) Patent No.: US 6,279,397 B1
(45) Date of Patent: Aug. 28, 2001

(54) METHOD AND APPARATUS FOR FOCUSING PROPAGATING WAVE PATHS OF A PHASED ARRAY IN SPHERICALLY-BOUNDED MATERIALS

(75) Inventor: Roger Francis Dwyer, Niantic, CT (US)

(73) Assignee: Westinghouse Electric Company LLC, Monroeville, PA (US)

( * ) Notice: Subject to any disclaimer, the term of this patent is extended or adjusted under 35 U.S.C. 154(b) by 0 days.

(21) Appl. No.: 09/441,890

(22) Filed: Nov. 17, 1999

(51) Int. Cl.[7] .................................................. G01N 29/00
(52) U.S. Cl. .............................. 73/606; 73/602; 73/626; 73/628; 600/443
(58) Field of Search ............................ 73/602, 625, 626, 73/628, 597, 598, 599, 600; 600/443, 444, 447; 376/252, 249

(56) References Cited

U.S. PATENT DOCUMENTS

| | | | |
|---|---|---|---|
| 4,317,369 | * | 3/1982 | Johnson ................................. 73/607 |
| 5,469,851 | * | 11/1995 | Lipschutz ............................... 73/626 |
| 5,549,002 | * | 8/1996 | Howard et al. ......................... 73/602 |
| 5,570,691 | * | 11/1996 | Wright et al. .......................... 73/626 |
| 5,591,911 | * | 1/1997 | Masuzawa et al. .................... 73/602 |
| 5,801,312 | * | 9/1998 | Lorraine et al. ....................... 73/602 |
| 6,020,988 | * | 2/2000 | Deliwala et al. ...................... 73/614 |

OTHER PUBLICATIONS

W. Gebhardt et al., Defect Reconstruction and Classification of Phased Arrays, Materials Evaluation 40, Jan. 1982, pp. 90–95.

K.H. Beck, Ultrasonic Transducer Focusing for Inspection of Cylindrical Material, TAC Technical Instrument Corp., Trenton, N.J., Oct. 1989, pp. 875–882.

\* cited by examiner

Primary Examiner—Daniel S. Larkin
Assistant Examiner—Jacques M. Saint-Surin
(74) Attorney, Agent, or Firm—Ronald P. Kananen; Rader, Fishman & Grauer (57) ABSTRACT

The present invention relates to a method and apparatus for focusing ultrasonic waves that are propagated from a phased array toward a spherically-bounded object so that they arrive at a pre-selected focal point at the same time and in phase and thereby significantly improve, nondestructively, the detectability of possible flaws in and structural characteristics of the object. The disclosed method comprises calculating the location of a plurality of preferred refraction points on a surface of the spherical work piece using an iterative process. Each of the preferred refraction points correspond to one of the elements of the phased array mechanism. The locations of the preferred refraction points depends upon the location of the pre-selected focal point and the locations of the phase elements. After the preferred refraction points are calculated, the method comprises calculating a pulse firing time for each element of the phased array mechanism that relates to the relative timing of the emitted waves from the elements.

22 Claims, 4 Drawing Sheets

METHOD AND APPARATUS FOR FOCUSING PROPAGATING WAVE PATHS OF A PHASED ARRAY IN SPHERICALLY-BOUNDED MATERIALS

BACKGROUND OF THE INVENTION

The present invention relates generally to the field of using ultrasonic waves to non-destructively detect structural characteristics of work pieces. More particularly, this invention relates to a method and apparatus for focusing ultrasonic waves that are propagated from a phased array to a spherically-bounded object so that the waves arrive at a pre-selected focal point at the same time and in phase and thereby significantly improve, nondestructively, the detectability of possible flaws in and structural characteristics of the object. Still more particularly, this invention relates to a method and apparatus for non-destructively evaluating spherically bounded objects, such as reactor pressure vessels, ball bearings, and the like by obtaining by iteration of a focal law equation according to the invention which follows a path on the surface of the spherically bounded object.

BRIEF DESCRIPTION OF THE PRIOR ART

The use of ultrasonic waves generally, and phased array mechanisms in particular, to nondestructively detect structural characteristics of work pieces is well known in the art. Generally, the technique consists of transmitting ultrasonic waves toward the work piece through various media such as water or air so that the waves impinge the surface of the workpiece, propagate throughout the internal structure of the work piece, and ultimately reflect back from the work piece. As the waves propagate throughout the work piece, they are reflected and refracted by variations and changes in the medium through which they travel. Defects in the structure of the work piece affect the travel path of the propagating waves. When the propagating waves reflect from the work piece, they are measured and analyzed. The structural characteristics of the work piece, including any defects or flaws, can be detected and reconstructed from the information contained in the reflected waves.

A phased array mechanism transmits ultrasonic waves from its multiple array elements which are spaced apart from each other. The waves are transmitted in a sequence at slightly different times relative to each other. The transmitted waves thus travel through a coupling material, which is usually water, prior to impinging the surface of the target work piece. Because of the molecular differences between the coupling material and the work piece, a portion of the propagating wave is reflected away from the work piece and a portion is refracted into the work piece. It is the refracted portion of each propagating wave that is used to detect and reconstruct structural defects and flaws of the work piece. The point at which the propagating waves impinge the work piece relative to their respective origination points partially determines the path of the refracted waves as they travel within the work piece.

In order to have the greatest ability to detect and reconstruct structural characteristics of the work piece, it is desirable for the refracted waves that enter and later exit the work piece to have the greatest possible amplitude. Waves that exit the work piece with a greater relative amplitude provide stronger and more readable signals.

It is well known that waves which arrive at a particular focal point at the same time and in phase constructively interfere with each other to create a wave with a larger relative amplitude. Accordingly, to improve the detection and reconstruction capabilities of phased arrays, it is desirable to focus all of the waves emitted from the elements of the phased array mechanism to create an internal wave with the greatest possible amplitude. To do so requires that all of the waves be focused and sequenced so that they arrive at a pre-selected focal point at the same time and in phase. However, until this invention, there was no way to determine the preferred refraction point on a spherical work piece or the proper sequence of transmitting pulses from the phased array so that the propagating waves arrived at a selected focal point at the same time and in phase in a work piece having a spherical boundary.

Accordingly, it is a continuing aim in the art to provide, in the field on nondestructive testing, a method and apparatus for determining the proper sequence of transmitted pulses in a phased array and a method and apparatus for visualizing the propagating wave paths in a spherically bounded material and contoured material that is spherical in the region being evaluated.

SUMMARY OF THE INVENTION

This invention comprises a method and apparatus to focus ultrasonic pulses transmitted from a phased array mechanism into a spherically-shaped work piece to increase the effectiveness of the non-destructive internal examination of the work piece. While this invention can be used with any spherical object, one such possible use is in connection with detecting internal flaws in nuclear reactor pressure vessel heads. To maximize the strength of the ultrasonic pulses when the pulses arrive at a particular selected focal point in the work piece, each pulse transmitted from an element of the phased array should be properly sequenced so that all of the pulses arrive at some selected focal point at the same time and in phase. In one aspect, the invention thus relates to a method and apparatus to determine to where the penetrating waves propagate to in the spherical work piece and how to properly sequence the transmitted pulses from all the phase elements comprising the phased array.

The method of the invention includes steps of determining location coordinates for preferred refraction points on the surface of the work piece that will direct impinging waves to arrive at a pre-selected focal point simultaneously. First, a focal point is pre-selected, and, accordingly, the location coordinates for the focal point are known before the method according to the invention is used. Second, the location coordinates for each element of the phased array are also known before the method according to the invention is used. Based upon the coordinates of the elements of the phased array mechanism and the pre-selected focal point, the coordinates for a desired refraction point on the surface of the work piece are calculated for each element of the phased array. In addition, a unique pulse firing time for each element of the phased array is calculated. The unique refraction point and pulse firing time for each array element permit the phased array to transmit the pulses from each element so that they all arrive at the focal point in phase and at the same time.

Each refraction point is uniquely determined relative to the center of the work piece by calculating two angles, $\theta_p$ and $\phi_p$, which together define a unique point on the surface of the work piece. The method of this invention includes an iterative calculation to determine $\theta_p$ and $\phi_p$. The values of $\theta_p$ and $\phi_p$ are referred to as $\theta_{p_i}$ and $\phi_{p_i}$ for each $i^{th}$ iteration of the method The method according to the invention begins by setting $\theta_i$ to an initial value between 0 and 360, preferably to 0. Based upon the initial selected value of $\theta_i$, the angle created by the line extending between the center of the work piece and the particular element of the phased array on the one hand, and the line extending between the center of the work piece and a potential refraction point on the other hand, is calculated. This angle is referred to as $\beta$. Then, the angle created by the line extending between the center of the work piece and the potential refraction point on the one hand, and the line extending between the center of the work piece and the pre-selected focal point on the other, is calculated. This angle is referred to as $\beta_f$. New values for $\theta_p$ and $\phi_p$ are calculated based upon the values of $\beta$ and $\beta_f$. The calculation of the new values for $\theta_p$ and $\phi_p$ require the analysis of several potential special case situations. The entire method is reiterated using a newly calculated initial value for $\theta_i$. The iteration process ceases when the value of $\theta_i$ and the values of $\theta_p$ and $\phi_p$ satisfy an equation, at which point, the final values for $\theta_p$ and $\phi_p$ are considered to be the last values of $\theta_p$ and $\phi_p$.

After the preferable refraction point is determined by $\theta_p$ and $\phi_p$, the preferable time delay for each array element is calculated based upon the coordinates of the refraction point, the coordinates of the element at issue, and the speed of sound.

The apparatus for performing the method according to the invention includes a work piece fixed at predetermined spatial location, a phased array, a microprocessor, and appropriate instrumentation.

DETAILED DESCRIPTION OF PREFERRED EMBODIMENTS OF THE INVENTION

Figure 1:
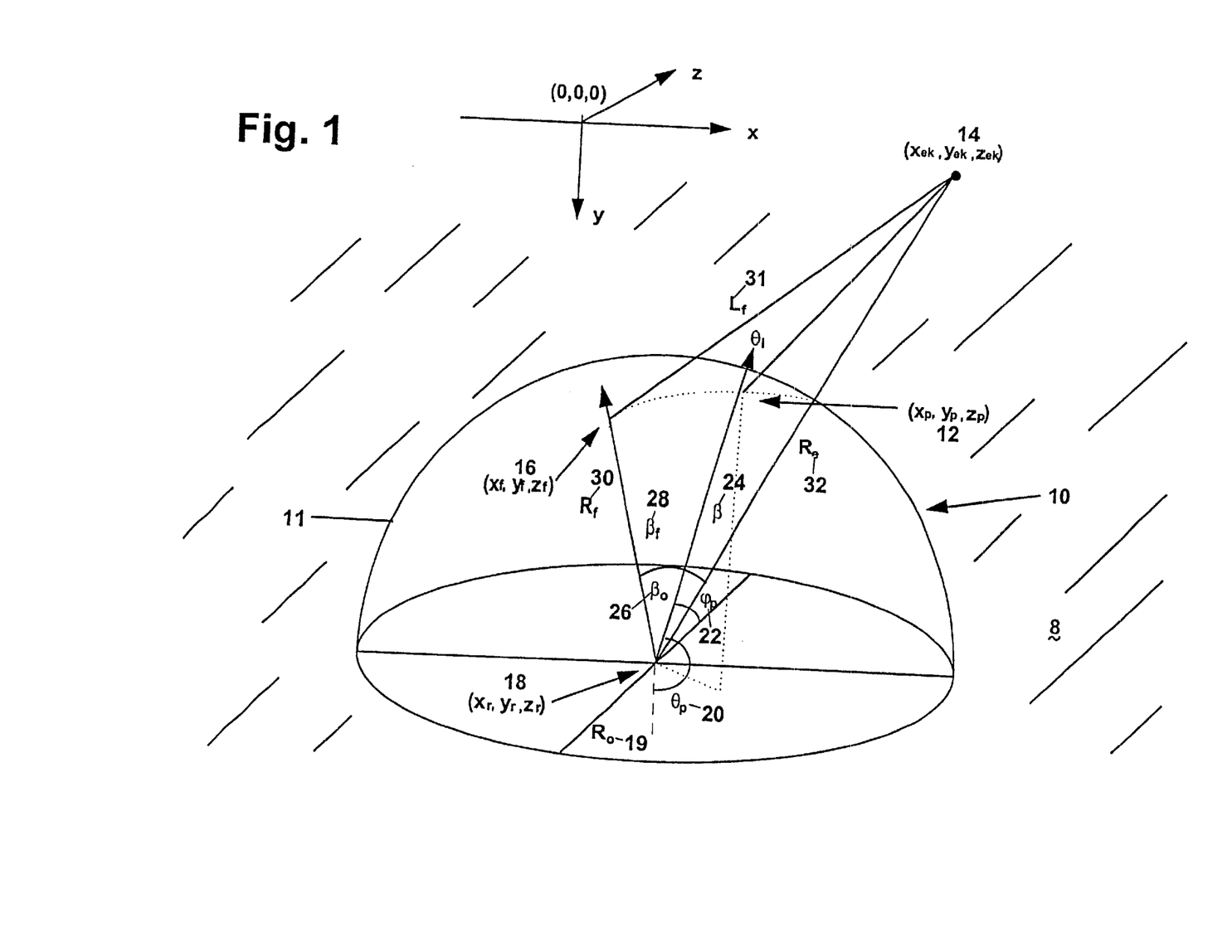
FIG. 1 is a perspective view of the environment, including the spherically-shaped boundary, in which the method according to the invention is used according to a first preferred embodiment.

FIG. 1 schematically and diagrammatically illustrates one possible environment in which the method and apparatus invention are used. With reference to FIG. 1, a spherically-bounded work piece 10 is surrounded by a coupling material 8. The coupling material 8 is usually water, but could be virtually any type of medium through which ultrasonic pulses can be transmitted and accurately detected. In the first embodiment of the invention, a phased array mechanism 14 is located outside of the spherically-bounded work piece 10, and it is surrounded by the coupling material 8. In a second embodiment of the invention, shown in FIG. 4, the phased array mechanism 14 may be located under the spherically-bounded work piece 10, depending upon the application. Regardless of the particular embodiment, the phased array mechanism 14 includes a plurality of transmitting phase elements. Each element of the phased array 14 is referred to as the "$k^{th}$ element" and its physical location is defined by a set of coordinates $(x_{ek}, y_{ek}, z_{ek})$. The phased array 14 can be a one-dimensional phased array, a two-dimensional phased array, or a three-dimensional phased array, depending on the application.

Figure 4:
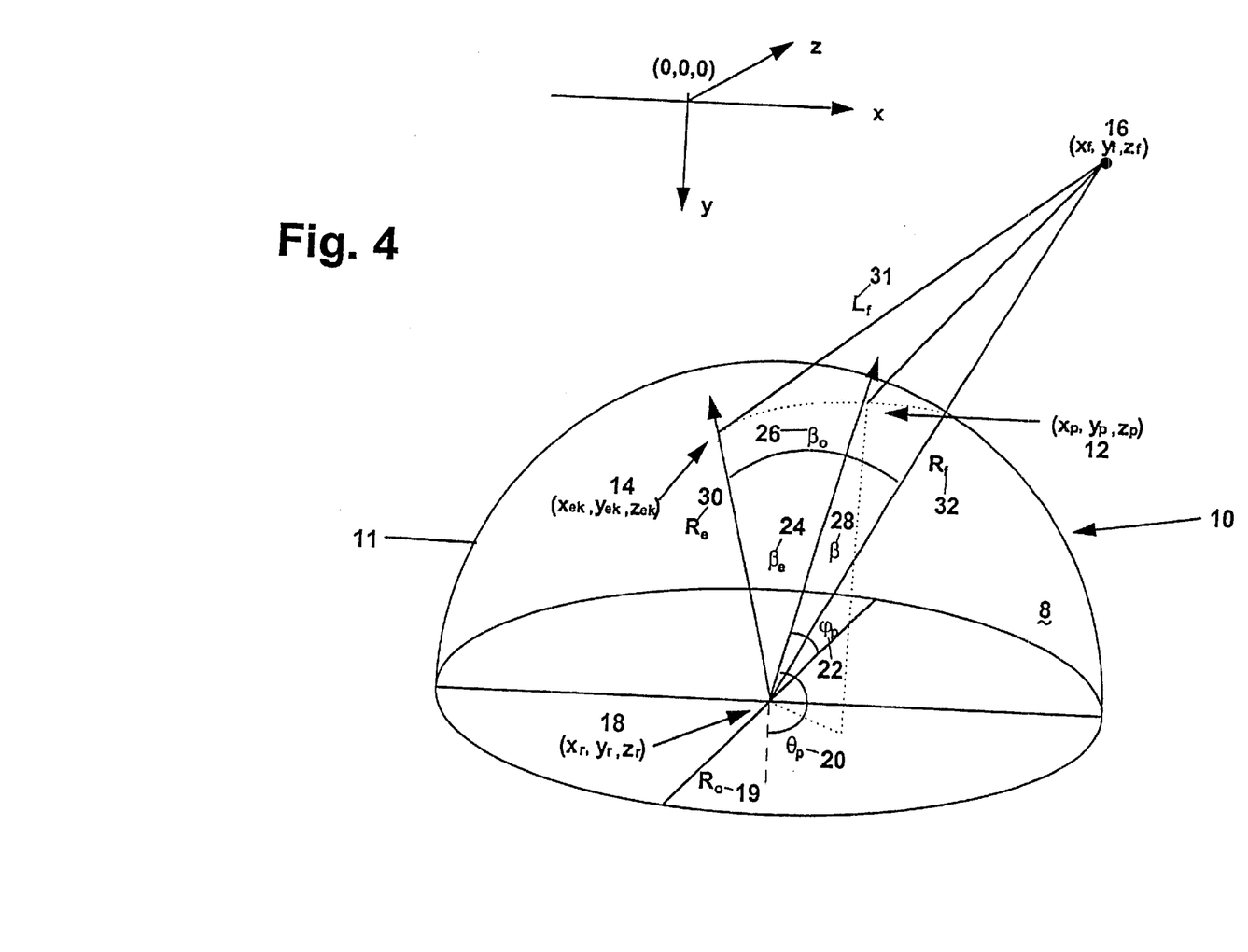
FIG. 4 is a perspective view of the environment, including the spherically-shaped boundary, in which the method according to the invention is used according to a second preferred embodiment.

Still referring to FIG. 1, the selected focal point 16 is located inside of work piece 10 in the first embodiment of the invention. In the second embodiment, as shown in FIG. 4, the focal point 16 is still located inside of the work piece 10. The coupling medium 8 surround the phased array 14. The selected focal point 16 is defined by a set of coordinates $(X_f, y_f, z_f)$. Based upon the location of the phased array elements 14 and the selected focal point 16, a unique preferred refraction point 12 is disposed on the bottom surface 11 of the work piece 10 for each element of the phased array. The specific locations of each of the refraction points 12 are defined by a set of coordinates, $(x_p, y_p, z_p)$. The location of the center 18 of the work piece 10 is defined by a set of coordinates, $(x_f, y_f, z_f)$.

FIG. 1 shows angles $\theta_p$ and $\phi_p$, which uniquely determine the refraction point 12. Unique values of $\theta_p$ and $\phi_p$ correspond to each of the individual locations of the phased array elements 14. Angle $\theta_p$ represents the location of refraction point 12 relative to the Y-axis, and angle $\phi_p$ represents the location of refraction point 12 relative to the Z-axis. The value of $\theta_p$ can vary between 0 and 360° and the value of $\phi_p$ can vary between 0 and 180°.

FIG. 1 also shows angles $\beta$, $\beta_f$, and $\beta^0$. Angle $\beta$ represents the angle created by the line extending between the work piece center 18 and the $k^{th}$ element of the phased array 14 on the one hand, and the line extending between the work piece center 18 and the refraction point 12 on the other. $\beta_f$ represents the angle created by the line extending between the work piece center 18 and the refraction point 12 on the one hand, and the line extending between the work piece center 18 and the selected focal point 16 on the other. Angle $\beta_0$ represents the sum of the angles $\beta$ and $\beta_f$.

FIG. 1 also shows line $R_0$, which represents the radius of the spherical work piece 10. Line $R_f$ represents the distance between the center 18 of the work piece 10 and the focal point 16. Finally, line $R_e$ represents the distance between the center 18 of the work piece 10 and the $k^{th}$ element of the phased array 14.

When the phased array 14 is operated, ultrasonic pulses from each of the elements of the phased array 14 are transmitted at various times relative to each other. Because of the relative spacing of the array elements, the waves are transmitted from somewhat different points of origination. The transmitted pulses propagate through the coupling material 8 and impinge upon the surface 11 of the spherical work piece 10, causing part of the wave to be reflected away from the surface 11 and causing a refracted portion of the wave to penetrate into the spherical work piece 10. The penetrating wave is used to detect flaws in the material. The elements comprising the phased array 14 can be omni-directional radiators or directional radiators. If the elements are directional radiators, those elements should be pointed towards the point on the surface 11 of the work piece 10 where the wave refracts into the work piece 10.

The given coordinates $(x_f, y_f, z_f)$ of the center 18 of the work piece 10 are known prior to beginning the invented method. Similarly, coordinates $(x_{ek}, y_{ek}, z_{ek})$ of each element of the phased array 14 are known prior to beginning the invented method. These coordinates are fixed values dictated by the respective physical locations of the work piece 10 and the phased array 14. The location of the preferred focal point 16 must be selected and the associated coordinates $(x_f, y_f, z_f)$ determined. The desired focal point 16 is selected either by the user of the method or by a computer algorithm. Once these given coordinate sets are determined, the method according to the invention is employed to determine $\theta_p$ and $\phi_p$ for each element of the phased array 14. The unique values of $\theta_p$ and $\phi_p$ identify the preferred refraction points 12 for each element of the phased array 14. After the preferred refraction points 12 are calculated, the proper sequencing and pulse firing times for the ultrasonic pulses emitted from the phased array 14 are calculated.

The basic premise of the method of the invention for locating the preferred refraction point 12 is to determine the unique plane that passes through the center of the sphere 18, the selected focal point 16, and the $k^{th}$ element, $(x_{ek}, y_{ek}, z_{ek})$ of the phased array 14. This plane will also contain the preferred refraction point 12, the location of which is defined by the coordinate set $(x_p, y_p, z_p)$ for the $k^{th}$ phase element.

Before the method of the invention can be described in detail, basic mathematical descriptions of the location coordinates of the refraction point 12, the focal point 16 and the phased array 14 are necessary.

The coordinates of the refraction point 12 for particular values of $\theta_p$ and $\phi_p$ that relate to a specific phase element can be described as, $$x_p = R_o \sin(\phi_p)\sin(\theta_p) + x_r$$
$$y_p = R_o \sin(\phi_p)\cos(\theta_d) + y_r$$
$$z_p = R_o \cos(\phi_p) + z_r,$$

where, $R_o$ is the known radius 19 of the sphere. These formulas are used to calculate specific coordinate values for each refraction point 12 after the values of $\theta_p$ and $\phi_p$ for each phase element are calculated using the method of the invention. The $k^{th}$ phase element position is defined as, $$x_e = R_e \sin(\phi_e)\sin(\theta_e) + x_r$$
$$y_e = R_e \sin(\phi_e)\cos(\theta_e) + y_r$$
$$z_e = R_e \cos(\phi_e) + z_r,$$

where, $R_e$ is the length of the line 32 from the center 18 of the work piece 10 to the $k^{th}$ element of the phased array 14. Similarly, the position of the focal point 16 is described as, $$x_f = R_f \sin(\phi_f)\sin(\theta_f) + x_r$$
$$y_f = R_f \sin(\phi_f)\cos(\theta_f) + y_r$$
$$z_f = R_f \cos(\phi_f) + z_r,$$

where, $R_f$ is the length of the line 30 from the center 18 of the work piece 10 to the given focal point 16.

Angles $\phi_e$ and $\theta_e$ are defined as follows:

$$\phi_e = \cos^{-1}[(z_e - z_r)/R_e],$$

For the principal values of the inverse tan function, if $(y_e - y_r) < 0$ and $(x_e - x_r) \geq 0$ then $\theta_e = 180° + \tan^{-1}[(x_e - x_r)/(y_e - y_r)]$ if $(y_e - y_r) > 0$ and $(x_e - x_r) \geq 0$ then $\theta_e = \tan^{-1}[(x_e - x_r)/(y_e - y_r)]$ if $(y_e - y_r) > 0$ and $(x_e - x_r) \leq 0$ then $\theta_e = 360° + \tan^{-1}[(x_e - x_r)/(y_e - y_r)]$ if $(y_e - y_r) < 0$ and $(x_e - x_r) \leq 0$ then $\theta_e = 180° + \tan^{-1}[(x_e - x_r)/(y_e - y_r)]$ if $(y_e - y_r) = 0$ and $(x_e - x_r) > 0$ then $\theta_e = 90°$ if $(y_e - y_r) = 0$ and $(x_e - x_r) < 0$ then $\theta_e = 270°$ Similarly the angles, $\phi_f$ and $\theta_f$ are defined as follows:

$$\phi_f = \cos^{-1}[(z_f - z_r)/R_f],$$

Figure 2:
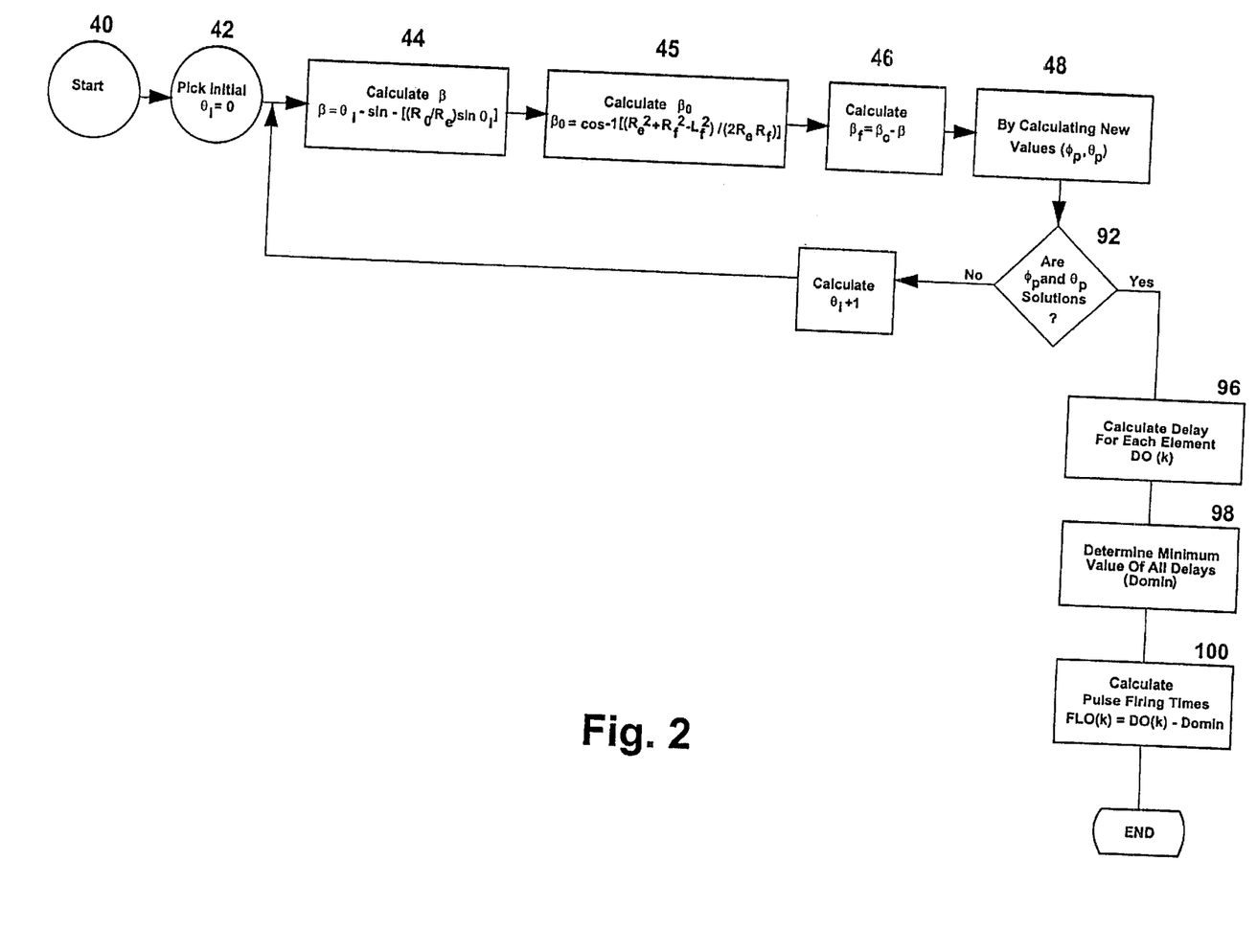
FIG. 2 is a detailed flowchart showing the steps of the method according to a preferred embodiment of the invention.

For the principal values of the inverse tan function, if $(y_f - y_r) < 0$ and $(x_f - x_r) \geq 0$ then $\theta_f = 180° + \tan^{-1}[(x_f - x_r)/(y_f - y_r)]$ if $(y_f - y_r) > 0$ and $(x_f - x_r) \geq 0$ then $\theta_f = \tan^{-1}[(x_f - x_r)/(y_f - y_r)]$ if $(y_f - y_r) > 0$ and $(x_f - x_r) \leq 0$ then $\theta_f = 360° + \tan^{-1}[(x_f - x_r)/(y_f - y_r)]$ if $(y_f - y_r) < 0$ and $(x_f - x_r) \leq 0$ then $\theta_f = 180° + \tan^{-1}[(x_f - x_r)/(y_f - y_r)]$ if $(y_f - y_r) = 0$ and $(x_f - x_r) > 0$ then $\theta_f = 90°$ if $(y_f - y_r) = 0$ and $(x_f - x_r) < 0$ then $\theta_f = 270°$ FIG. 2 shows a flowchart which sets forth the steps that comprise the method according to the invention for calculating angles $\theta_p$ and $\phi_p$ for the pre-selected focal point 16, as well as for calculating the preferred pulse firing times of each phase element. The invented method is an iterative process. After the method is started at step 40, an initial trial value for $\theta_i$ is selected at step 42. The value for $\theta_i$ used in each pass of the iterative method is referred to as $\theta_i$, where i represents the number of times that the iterative process has been repeated. In the disclosed embodiment, the initial value for $\theta_i$ (or $\theta_o$) is 0. After the initial $\theta_i$ value is chosen, $\beta$ is calculated at step 44 according to the following formula:

$$\beta = \theta_i - \sin^{-1}[(R_o/R_e)\sin(\theta_i)]. \quad (1)$$

Then, $\beta_o$ is calculated at step 45 according to the following formula:

$$\beta_o = \cos^{-1}[(R_e^2 + R_f^2 - L_f^2)/(2R_eR_f)]. \quad (2)$$

where, $R_e$ is the length of the line 32 from the center 18 of the spherical work piece 10 to the $k^{th}$ element of the phased array 14, $R_f$ is the length of the line 30 from the center 18 of the spherical work piece 10 to the focal point 16, and $L_f$ is the length of the line 31 from the focal point 16 to the $k^{th}$ element of the phased array 14. These variables can be defined further as, $R_e = [(x_{ek} - x_r)^2 + (y_{ek} - y_r)^2 + (z_{ek} - z_r)^2]^{1/2}$, $R_f = [(x_f - x_r)^2 + (y_f - y_r)^2 + (z_f - z_r)^2]^{1/2}$, and $L_f = [(x_{ek} - x_f)^2 + (y_{ek} - y_f)^2 + (z_{ek} - z_f)^2]^{1/2}$.

After $\beta$ and $\beta_o$ are calculated, $\beta_f$ is calculated at step 46 of FIG. 2 according to the following formula:

$$\beta_f = \beta_o - \beta. \quad (3)$$

Figure 3:
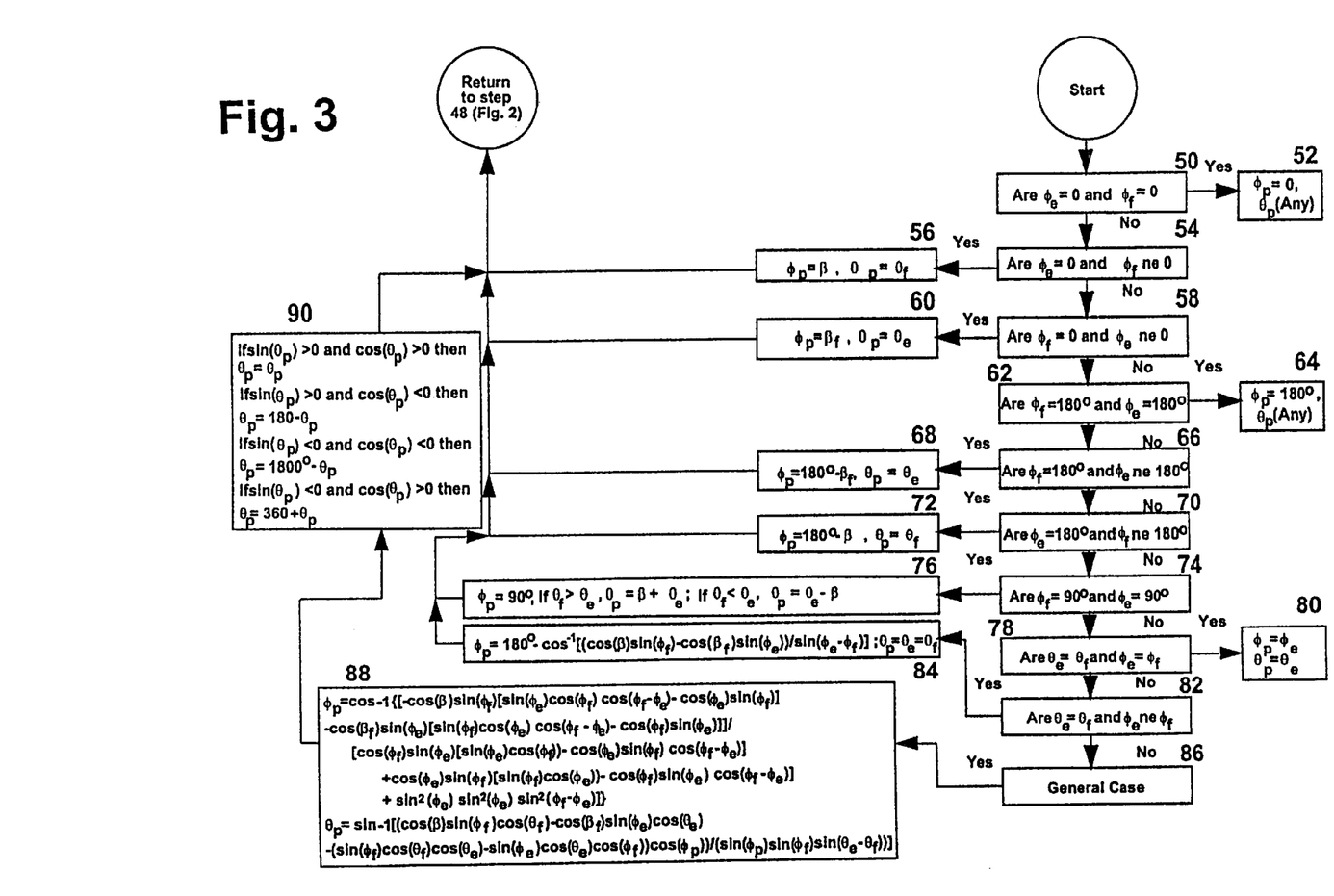
FIG. 3 is a detailed flowchart showing the steps of the method according to the invention associated with calculating values for $\theta_p$ and $\phi_p$ according to a preferred embodiment.

Once $\beta$ and $\beta_f$ are calculated in steps 44 and 46 for the initial value of $\theta_i$, the following equations (4) and (5) are solved for new values of angles $\theta_p$ and $\phi_p$ in step 48:

$$\cos(\beta) = \sin(\phi_e)\sin(\theta_e)\sin(\phi_p)\sin(\theta_p) + \sin(\phi_e)\cos(\theta_e)\sin(\phi_p)\cos(\theta_p) + \cos(\phi_e)\cos(\phi_p) \quad (4)$$

and $$\cos(\beta_f) = \sin(\phi_f)\sin(\theta_f)\sin(\phi_p)\sin(\theta_p) + \sin(\phi_f)\cos(\theta_f)\sin(\phi_p)\cos(\theta_p) + \cos(\phi_f)\cos(\phi_p), \quad (5)$$

where, $(\phi_e, \theta_e)$, and $(\phi_f, \theta_f)$ are the angles that give the position of the $k^{th}$ element of phased array 14 and focal point 16, respectively, with respect to the center 18 of the spherical work piece 10. The method for solving these equations for the new values of $\theta_p$ and $\phi_p$ is shown in detail in FIG. 3, which illustrates in detail the substeps that comprise step 48 in FIG. 2.

Referring to FIG. 3, there are several special cases of solutions to equations (4) and (5). Each one of these special cases must be reviewed and evaluated prior to solving equations (4) and (5) according to the general case. If one of the special cases apply, then the values for $\theta_p$ and $\phi_p$ will have pre-defined values. If none of the special cases apply, then the values of $\theta_p$ and $\phi_p$ will be determined according to the general case. Each of the special cases and the general case, along with their associated solutions, are as follows:

Special case 1 (steps 50, 52)
IF $\phi_e=0$ and $\phi_f=0$
THEN $\phi_p=0$ and $\theta_p$ is arbitrary (any angle will satisfy)
Special case 2 (steps 54, 56)
IF $\phi_e=0$, $\phi_f\neq 0$, and $\phi_f\neq 180°$
THEN $\phi_p=\beta\neq 0$, and $\theta_p=\theta_f$
Special case 3 (steps 58, 60)
IF $\phi_e\neq 0$, $\phi_f=0$ and $\phi_e\neq 180°$
THEN $\phi_p=\beta_f\neq 0$, and $\theta_p=\theta_e$
Special case 4 (steps 62, 64)
IF $\phi_e=180°$ and $\phi_f 180°$
THEN $\phi_p=180°$ and $\theta_p$ is arbitrary (any angle will satisfy)
Special case 5 (steps 66, 68)
IF $\phi_e=180°$, $\phi_f\neq 180°$ and $\phi_f\neq 0°$
THEN $\phi_p=180°-\beta$, $\beta\neq 0°$ and $\theta_p=\theta_f$
Special case 6 (steps 70, 72)
IF $\phi_f=180°$, $\phi_e\neq 180°$, and $\phi_e\neq 0°$
THEN $\phi_p=180°-\beta_f$, and $\theta_p=\theta_e$
Special case 7 (steps 74, 76)
IF $\phi_e=90°$ and $\phi_f=90°$
THEN $\phi_p=90°$, and if $\theta_f>\theta_e$ then $\theta_p=\beta+\theta_e$ or $\theta_p=\theta_f-\beta_f$ if $\theta_f<\theta_e$ then $\theta_p=\theta_e-\beta$ or $\theta_p=\beta_f+\theta_f$ Special case 8 (steps 78, 80)
IF $\theta_e=\theta_f$ and $\phi_e=\phi_f\neq 0$
THEN $\phi_p=\phi_e=\phi_f$ and $\theta_p=\theta_e=\theta_f$
Special case 9 (steps 82, 84)
IF $\theta_e=\theta_f$, $\phi_e\neq\phi_f$ and $\phi_p\neq 0$
THEN $\phi_p=180°-\cos^{-1}[\{\cos(\beta)\sin(\phi_f)-\cos(\beta_f)\sin(\phi_e)\}/\{\sin(\phi_e-\phi_f)\}]$ and $\theta_p=\theta_e=\theta_f$
General case (steps 86, 88)
IF $\phi_e\neq 0$, $\phi_f\neq 0$, $\phi_e\neq 180°$, $\phi_f\neq 180°$, and $\theta_e\neq\theta_f$
THEN $\phi_p=\cos^{-1}[-B/A]$
where, $B=\cos(\beta)\sin(\phi_f)[\sin(\phi_e)\cos(\phi_f)\cos(\theta_f-\theta_e)-\cos(\phi_e)\sin(\phi_f)]+\cos(\beta_f)\sin(\phi_e)[\sin(\phi_f)\cos(\phi_e)-\cos(\phi_f)\sin(\phi_e)]$ and, $A=\cos(\phi_f)\sin(\phi_e)[\sin(\phi_e)\cos(\phi_f)-\cos(\phi_e)\sin(\phi_f)\cos(\theta_f-\theta_e)]$ $+\cos(\phi_e)\sin(\phi_f)[\sin(\phi_f)\cos(\phi_e)-\cos(\phi_f)\sin(\phi_e)\cos(\theta_f-\theta_e)]$ $+\sin^2(\phi_e)\sin^2(\phi_f)\sin^2(\theta_f-\theta_e)\theta_p=\sin^{-1}\{[\cos(\beta)\sin(\phi_f)\cos(\theta_f)-\cos(\beta_f)\sin(\phi_e)\cos(\theta_e)$ $-(\sin(\phi_f)\cos(\theta_f)\cos(\theta_e)-\sin(\phi_e)\cos(\theta_e)\cos(\phi_f)\cos(\phi_p)]/(\sin(\phi_p)\sin(\phi_f)\sin(\phi_e)\sin(\theta_e-\theta_f))\}$ Thus, new values of $\theta_p$ and $\phi_p$ are calculated for the $i^{th}$ iteration of the invented method in step 48 of FIG. 2 according to substeps 50 through 88 shown in FIG. 3.

After $\theta_p$ and $\phi_p$ are calculated according to step 48, it is necessary to determine, as shown in step 90 of FIG. 3, which quadrant $\theta_p$ is in to determine the actual value for $\theta_p$ for the $i_{th}$ iteration of the invented method. The final value of $\theta_p$ is determined in step 90 according to the following rules:

If $\sin(\theta_p)>0$ and $\cos(\theta_p)>0$, then $\theta_p=\theta_p$

If $\sin(\theta_p)>0$ and $\cos(\theta_p)<0$, then $\theta_p=180-\theta_p$

If $\sin(\theta_p)<0$ and $\cos(\theta_p)<0$, then $\theta_p=180-\theta_p$

If $\sin(\theta_p)<0$ and $\cos(\theta_p)>0$, then $\theta_p=360+\theta_p$

After $\phi_p$ and $\theta_p$ are calculated for the $i^{th}$ iteration of the invented method, they are checked to determine if the point that they define on the surface 11 of the spherical work piece 10 is a solution in that the refracted portion of the transmitted pulse actually propagates to the selected focal point 16. This task is shown in step 92 of FIG. 2. The point defined by $\phi_p$ and $\theta_p$ is a solution, and thus defines the location of the preferred refraction point 12 for the particular phase element being considered, if it satisfies the following equation:

$$BB=U_1\mathrm{Tan}(\theta_i)+U_2\mathrm{Tan}(\theta_1) \qquad (6)$$

where, $\theta_r=\sin^{-1}[(c_2/c_1)\sin(\theta_i)]$ and c1 and c2 are the speed of sound in the coupling material and the speed of sound in the spherically bounded material, respectively. The other parameters in equation (10) are defined as follows:

$BB=X_1+X_2$, $X_1=[(x_p-x_1)^2+(y_p-y_1)^2+(z_p-z_1)^2]^{1/2}$ $X_2=[(x_p-x_2)^2+(y_p-y_2)^2+(z_p-z_2)^2]^{1/2}$ $U_1=[(x_{ei}-x_1)^2+(y_{ei}-y_1)^2+(z_{ei}-z_1)_2]^{1/2}$ $U_2=[(x_f-x_2)^2+(y_f-y_2)^2+(z_f-z_2)^2]^{1/2}$ and the components are given by, $x_1=(\cos^2(\theta_p)+\cos^2(\phi_p)\sin^2(\theta_p))x_e-\sin^2(\phi_p)\sin(\theta_p)\cos(\theta_p)y_e-\sin(\phi_p)\cos(\phi_p)\sin(\theta_p)z_e$ $+\sin^2(\phi_p)\sin^2(\theta_p)x+\sin^2(\phi_p)\sin(\theta_p)\cos(\theta_p)y_p+\sin(\phi_p)\cos(\phi_p)\sin(\theta_p)z_p$ $y_1=-\sin^2(\phi_p)\sin(\theta_p)\cos(\theta_p)x_e+(\cos^2(\theta_p)\cos^2(\theta_p)+\sin^2(\theta_p))y_e-\sin(\phi_p)\cos(\phi_p)\sin(\theta_p)z_e$ $+\sin^2(\phi_p)\sin(\theta_p)\cos(\theta_p)x_p+\sin^2(\phi_p)\cos^2(\theta_p)y_p+\sin(\phi_p)\cos(\phi_p)\cos(\theta_p)z_p$ $z_1=\sin(\phi_p)\sin(\theta_p)\cos(\phi_p)(x_p-x_e)+\sin(\phi_p)\cos(\phi_p)\cos(\theta_p)(y_p-y_e)+\cos^2(\phi_p)(z_p-z_e)+z_e$ $x_2=(\cos^2(\theta_p)+\cos^2(\phi_p)\sin^2(\theta_p))x_f-\sin^2(\phi_p)\sin(\theta_p)\cos(\theta_p)y_f-\sin(\phi_p)\cos(\phi_p)\sin(\theta_p)z_f+$ $\sin^2(\phi_p)\sin^2(\theta_p)x_f+\sin^2(\phi_p)\sin(\theta_p)y_p+\sin(\phi_p)\cos(\phi_p)\sin(\theta_p)z_p$ $y_2=-\sin^2(\phi_p)\sin(\theta_p)\cos(\theta_p)x_f+(\cos^2(\phi_p)\cos^2(\theta_p)+\sin^2(\theta_p))y_f-\sin(\phi_p)\cos(\phi_p)\sin(\theta_p)z_f+$ $\sin(\phi_p)\sin(\theta_p)\cos(\theta_p)x_p+\sin^2(\phi_p)\cos^2(\theta_p)y_p+\sin(\phi_p)\cos(\phi_p)\cos(\theta_p)z_p$ $z_2=\sin(\phi_p)\sin(\theta_p)\cos(\phi_p)(x_p-x_f)+\sin(\phi_p)\cos(\phi_p)\cos(\theta_p)(y_p-y_f)+\cos^2(\phi_p)(z_p-z_f)+z_f$ The values of $\theta_p$ and $\phi_p$ are considered to satisfy equation (6) if equation (6) has converged sufficiently with respect to previous values of $\phi_p$ and $\theta_p$. That is, $\phi_p$ and $\theta_p$ are considered to define the location of the preferred focal point 16 if $$\text{test\_error} > U_1 \tan(\theta_i) + U_2 \tan(\theta_i) - BB,$$

where test_error is a pre-selected allowable margin of error.

If the current values of $\theta_p$ and $\phi_p$ do not constitute a solution, then the disclosed method is iterated according to a modified version of Newton's well-known root finding technique. A new $\theta_{i+1}$ is calculated, as set forth in step 94 according to the following equations:

$$f\text{test} = U_1 \tan(\theta_i) + U_2 \tan(\theta_i) - BB$$

$$f\text{test} = (U_1/\cos(\theta_i)^2) + (U_2/\cos(\theta_i)^2)((c2/c1)\cos(\theta_i))/[1-((c2/c1)\sin(\theta_i))^2]^{1/2}$$

$$\theta_{i+1} = \theta_i - \text{delta}(f\text{test}/f\text{test})$$

where delta is a pre-selected value. The value of delta may be selected by the user of the method or by a computer algorithm.

As stated, the entire iteration process stops when equation (6) converges. When equation (6) converges, $\theta_p$ and $\phi_p$ define the preferred refraction point 12 and the current angles $\theta_p$ and $\phi_p$ are considered to be $\theta_p$ and $\phi_p$. The iteration process may also be designed to cease after a maximum number of iterations if a solution is not found before.

Once the preferred refraction point 12 is determined, the associated pulse firing times are calculated as shown in step 96. The element delays, do(k), for each element k of a phased array 14 located above the spherical work piece 10 is calculated as follows:

$$do(k) = (ro_1 - ro_1(k))/c_1 + (ro_2 - ro_2(k))/c_2$$

where, $ro_1 = [(x_c - x_{p0})^2 + (y_c - y_{p0})^2 + (z_c - z_{p0})^2]^{1/2}$, $(x_c, y_c, z_c)$ are the coordinates of the center of the phased array, $(x_{p0}, y_{p0}, z_{p0})$ is the point on the surface 11 of the spherical work piece 10 where a wave propagated from the center of the phased array 14 would refract toward the focal point 16, $ro_1(k) = [(x_{pk} - x_{ek})^2 + (y_{pk} - y_{ek})^2 + (z_{pk} - z_{ek})^2]^{1/2}$, $(x_{pk}, y_{pk}, z_{pk})$ is the point on the surface 11 where the wave from the $k^{th}$ element refracts towards the focal point 16, $ro_2 = [(x_f - x_{p0})^2 + (y_f - y_{p0})_2 + (z_f - z_{p0})^2]^{1/2}$, $(x_f, y_f, z_f)$ is the focal point, and $ro_2(k) = [(x_f - x_{pk})^2 + (y_f - y_{pk})^2 + (z_f - z_{pk})^2]^{1/2}$. After the time delay, do(k), has been calculated for each of the k phase elements, the minimum time delay, domin, is identified from the set of all time delays, do(k). This task is shown in step 98 of FIG. 2. Finally, as set forth in step 100, the focal law sequence, FLO(k), for all of the k phase elements is calculated by subtracting the identified minimum time delay, domin, from all of the element time delays, do(k). That is, FLO(k)=do(k)−domin. Thus, for each phase element, k, FLO(k) provides the preferred pulse firing times.

As already noted, a second embodiment of this invention is shown in FIG. 4 where phased array 14 is located on the other side of the spherical work piece 10. In this second embodiment, the focal point 16 is located inside of the spherical work piece 10 as before. Otherwise, the components and configuration of the environment where the disclosed invention is used is the same as the first embodiment. The same methodology as described above and shown in the flowcharts in FIGS. 2 and 3 is used to determine each preferred refraction point 12 corresponding to the various phase elements. That is, the methodology depends upon the following relationship:

$$\beta_e = \beta_0 - \beta$$

The only difference in the second embodiment shown in FIG. 2 relating to the calculation of the preferred refraction point 12 is that the mathematical definition of $\beta_e$ is as follows:

$$\beta_e = \theta_i - \sin^{-1}[(R_0/R_f)\sin(\theta_i)].$$

In contrast, in the first embodiment shown in FIG. 1, $\beta$ is defined by this formula.

A second difference between the first and second embodiments relates to the method of determining the timing sequence for the k phase elements. As in the first embodiment, the preferred time delay for each phase element is calculated (step 96) after the various preferred refraction points 12 are determined, as in steps 48 through 94. When the disclosed invention is used in an environment where the phased array 14 is located on the other side of the spherical work piece 10, the preferred delay associated with the $k^{th}$ phase element is defined as follows:

$$di(k) = (ri_1 - ri_1(k))/c_1 + (ri_2 - ri_2(k))/c_2,$$

where, $c_1$ is the speed of sound in the material comprising the spherical work piece 10 and $c_2$ is the speed of sound in the coupling material 8. The other parameters are, $ri_1 = [(x_f - x_{po})^2 + (y_f - y_{po})^2 + (z_f - z_{po})^2]^{1/2}$, $(x_{po}, y_{po}, z_{po})$ is the point on the inside surface 11 where a wave propagated from the focal point 16 would refract toward the center of the array, $ri_1(k) = [(x_{pk} - x_f)^2 + (y_{pk} - y_f)^2 + (z_{pk} - z_f)^2]^{1/2}$, $(x_{pk}, y_{pk}, z_{pk})$ is the point on the inside surface where the wave from the focal point refracts towards the $k^{th}$ element, $ri_2 = [(x_{ek} - x_{pk})^2 + (y_{ek} - y_{pk})_2 + (z_{ek} - z_{pk})^2]^{1/2}$, $(x_{ek}, y_{ek}, z_{ek})$ is the $k^{th}$ element, and $ri_2(k) = [(x_{ek} - x_{pk})^2 + (y_{ek} - y_{pk})^2 + (z_{ek} - z_{pk})^2]^{1/2}$. Except for the two identified differences, the methodology for determining preferred refraction points and delay times is the same whether the phased array is located above or on the other side of the spherical work piece 10.

While preferred embodiments of the present invention have been described herein, it is apparent that the basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

What is claimed is:

1. A method for focusing ultrasonic waves emitted from a plurality of elements of a phased array mechanism and directed toward a spherical work piece, having a surface and a center, to arrive at a pre-selected focal point at the same time and in phase, comprising the steps of:

calculating the location of at least one of a plurality of preferred refraction points on a surface of the spherical work piece using an iterative process, each of said preferred refraction points corresponding to one of the elements of the phased array mechanism and each of said preferred refraction points being uniquely defined relative to the location of the center of the spherical work piece by a first angle, $\theta_p$, representing a rotation about a first spatial axis, and a second angle, $\phi_p$, representing a rotation about a second spatial axis; and     calculating a pulse firing time for each element of the phased array mechanism that relates to the relative timing of the emitted waves from the elements.

2. The method of claim 1, wherein the step of calculating the location of at least one of the preferred refraction points comprises the substeps of:

a) choosing an initial value for $\theta_i$ corresponding to one element of the phased array mechanism where (i) represents the number of times that the iterative process has been repeated and $\theta_0$ represents a preselected initial angle, for the beginning of the iterative process;

b) calculating new values for $\theta_p$ and $\phi_p$ based upon said initial value of $\theta_i$, said new values of $\theta_p$ and $\phi_p$ defining the location of a potential refraction point corresponding to said one element;

c) determining if said calculated new values for $\theta_p$ and $\phi_p$ define a point on the surface of the spherical work piece such that a wave emitted from said one element passes through the pre-selected focal point; and d) if said calculated new values for $\theta_p$ and $\phi_p$ do not define a point on the surface of the spherical work piece such that a wave emitted from said one element passes through the pre-selected focal point, then calculating a new initial value for $\theta_{(i+1)}$ as a function of a pre-selected incremental factor and the value $\theta_i$ then incrementing (i) and repeating substeps (b) through (d) with the new value $\theta_i$.

3. The method of claim 2, wherein the step of calculating new values for $\theta_p$ and $\phi_p$ is a function of angles $\phi_e$, $\theta_e$, $\phi_f$, $\theta_f$, said angles $\phi_e$, $\theta_e$ defining the location of said one element of said phased array relative to the center of the spherical work piece, and said angles $\phi_f$, $\theta_f$ defining the location of the focal point relative to the center of the spherical work piece.

4. The method of claim 3, wherein the step of calculating new values for $\theta_p$ and $\phi_p$ is further a function of angles $\beta$ and $\beta_f$, said angle $\beta$ constituting an angle formed by a line extending between the center of the spherical work piece and said one element of the phased array mechanism and a line extending between the center of the spherical work piece and said potential refraction point.

5. The method of claim 4, wherein angle $\beta$ is calculated according to the formula, $\beta = \theta_i - \sin^{-1}[(R_0/R_e)\sin(\theta_i)]$, where $R_0$ is the radius of the spherical work piece and $R_e$ is the distance between the center of the spherical work piece and said element of the phased array.

6. The method of claim 4, wherein the step of calculating new values for $\theta_p$ and $\phi_p$ comprises the following steps:

(i) determining if $\phi_e=0$ and $\phi_f=0$, and, if so, assigning $\phi_p=0$ and assigning $\theta_p$ equal to any arbitrary value;

(ii) determining if $\phi_e=0$ and $\phi_f\neq 0$ and $\phi_f\neq 180°$, and, if so, then assigning $\phi_p=\beta$ and assigning $\theta_p=\theta_f$;

(iii) determining if $\phi_e\neq 0$ and $\phi_f=0$ and $\phi_e\neq 180°$, and, if so, then assigning $\phi_p=\beta_f$ and assigning $\theta_p=\theta_e$;

(iv) determining if $\phi_e=180°$ and $\phi_f=180°$, and, if so, assigning $\phi_p=180°$ and assigning $\theta_p$ to any arbitrary value;

(v) determining if $\phi_e=180°$ and $\phi_f\neq 180°$ and $\phi_f\neq 0°$, and, if so, assigning $\phi_p=180°-\beta$ and assigning $\theta_p=\theta_f$;

(vi) determining if $\phi_f=180°$ and $\phi_e\neq 180°$ and $\phi_e\neq 0°$, and, if so, assigning $\phi_p=180°-\beta_f$ and assigning $\theta_p=\theta_e$;

(vii) determining if $\phi_e=90°$ and $\phi_f=90°$ and $\theta_f>\theta_e$, and, if so, assigning $\phi_p=90°$ and assigning $\theta_p=\beta+\theta_e$;

(viii) determining if $\phi_e=90°$ and $\phi_f=90°$ and $\theta_f<\theta_e$, and, if so, assigning $\phi_p=90°$ and assigning $\theta_p=\theta_e-\beta$;

(ix) determining if $\theta_e=\theta_f$ and $\phi_e=\phi_f$ and $\phi_f\neq 0$, and, if so, assigning $\phi_p=\phi_e$ and assigning $\theta_p=\theta_e$;

(x) determining if $\theta_e=\theta_f$ and $\phi_e\neq\phi_f$ and $\phi_f\neq 0$, and, if so, assigning $\theta_p=\theta_e$ and assigning $\phi_p=180°-\cos^{-1}[\{\cos(\beta)\sin(\phi_f)-\cos(\beta_f)\sin(\phi_e)\}/\{\sin(\phi_e-\phi_f)\}]$;

if none of the conditions in steps (i) through (x) are satisfied, then assigning values to $\theta_p$ and $\phi_p$ as a function of $\phi_e$, $\theta_e$, $\phi_f$, $\theta_f$.

7. The method of claim 6, wherein the step of assigning values to $\theta_p$ and $\phi_p$ as a function of $\phi_e$, $\theta_e$, $\phi_f$, $\theta_f$ comprises the steps:

assigning $\phi_p=\cos^{-1}[-B/A]$ where, $B=\cos(\beta)\sin(\phi_f)[\sin(\phi_e)\cos(\phi_f)\cos(\theta_f-\theta_e)-\cos(\phi_e)\sin(\phi_f)]$ $+\cos(\beta_f)\sin(\phi_e)[\sin(\phi_f)\cos(\phi_e)\cos(\theta_f-\theta_e)-\cos(\phi_f)\sin(\phi_e)]$ and $A=\cos(\phi_f)\sin(\phi_e)[\sin(\phi_e)\cos(\phi_f)-\cos(\phi_e)\sin(\phi_f)\cos(\theta_f-\theta_e)]$ $+\cos(\phi_e)\sin(\phi_f)[\sin(\phi_f)\cos(\phi_e)-\cos(\phi_f)\sin(\phi_e)\cos(\theta_f-\theta_e)]$ $+\sin^2(\phi_e)\sin^2(\phi_f)\sin^2(\theta_f-\theta_e)$; and assigning $\theta_p=\sin^{-1}\{[\cos(\beta)\sin(\phi_f)\cos(\theta_f)-\cos(\beta_f)\sin(\phi_e)\cos(\theta_e)-(\sin(\phi_f)\cos(\theta_f)\cos(\theta_e)-\sin(\phi_e)\cos(\theta_e)\cos(\phi_f))\cos(\phi_p)]/(\sin(\phi_p)\sin(\phi_f)\sin(\phi_e)\sin(\theta_e-\theta_f))\}$.

8. The method of claim 7, wherein the step of calculating new values for $\theta_p$ and $\phi_p$ further comprises the step of adjusting the value of $\theta_p$ according to the following conditions:

If $\sin(\theta_p)>0$ and $\cos(\theta_p)>0$, then $\theta_p=\theta_p$;
If $\sin(\theta_p)>0$ and $\cos(\theta_p)<0$, then $\theta_p=180-\theta_p$;
If $\sin(\theta_p)<0$ and $\cos(\theta_p)<0$, then $\theta_p=180-\theta_p$; and
If $\sin(\theta_p)<0$ and $\cos(\theta_p)>0$, then $\theta_p=360+\theta_p$.

9. The method of claim 2, wherein the step of calculating said pulse firing time for each element of the phased array mechanism comprises the substeps:

calculating an element delay value for each element of the phased array mechanism;

determining the minimum value of all of said element delay values;

subtracting said minimum value from each of said element delay values.

10. A method for focusing ultrasonic waves emitted from a plurality of elements of a phased array mechanism and directed toward a spherical nuclear reactor pressure vessel head, having a surface and a center, to arrive at a preselected focal point at the same time and in phase, comprising the steps of:

calculating the location of at least one of a plurality of preferred refraction points on a surface of the spherical vessel head using an iterative process, each of said preferred refraction points corresponding to one of the elements of the phased array mechanism and each of said preferred refraction points being uniquely defined relative to the location of the center of the spherical vessel head by a first angle, $\theta_p$, representing a rotation about a first spatial axis, and a second angle, $\phi_p$, representing a rotation about a second spatial axis; and calculating a pulse firing time for each element of the phased array mechanism that relates to the relative timing of the emitted waves from the elements.

11. The method of claim 10, wherein the step of calculating the location of at least one of the preferred refraction points comprises the substeps of:

a) choosing an initial value for $\theta_i$ corresponding to one element of the phased array mechanism where (i) represents the number of times that the iterative process has been repeated and $\theta_0$ represents a preselected initial angle, for the beginning of the iterative process;

b) calculating new values for $\theta_p$ and $\phi_p$ based upon said initial value of $\theta_i$, said new values of $\theta_p$ and $\phi_p$ defining the location of a potential refraction point corresponding to said one element;

c) determining if said calculated new values for $\theta_p$ and $\phi_p$ define a point on the surface of the spherical work piece such that a wave emitted from said one element passes through the pre-selected focal point; and d) if said calculated new values for $\theta_p$ and $\phi_p$ do not define a point on the surface of the spherical work piece such that a wave emitted from said one element passes through the pre-selected focal point, then calculating a new initial value for $\theta_{(i+1)}$ as a function of a pre-selected incremental factor and the value $\theta_i$ then incrementing (i) and repeating substeps (b) through (d) with the new value $\theta_i$.

12. An apparatus for focusing ultrasonic waves emitted from a plurality of elements of a phased array mechanism and directed toward a spherical work piece, having a surface and a center, to arrive at a pre-selected focal point at the same time and in phase, comprising:

location calculating means for calculating the location of at least one of a plurality of preferred refraction points on a surface of the spherical work piece using an iterative process, each of said preferred refraction points corresponding to one of the elements of the phased array mechanism and each of said preferred refraction points being uniquely defined relative to the location of the center of the spherical work piece by a first angle, $\theta_p$, representing a rotation about a first spatial axis, and a second angle, $\phi_p$, representing a rotation about a second spatial axis; and pulse firing time means for calculating a pulse firing time for each element of the phased array mechanism that relates to the relative timing of the emitted waves from the elements.

13. The apparatus of claim 12, wherein the location calculating means for calculating the location of at least one of the preferred refraction points further comprises:

a) means for receiving an initial value for $\theta_i$ corresponding to one element of the phased array mechanism where (i) represents the number of times that the iterative process has been repeated and $\theta_0$ represents a preselected initial angle, for the beginning of the iterative process;

b) means for calculating new values for $\theta_p$ and $\phi_p$ based upon said initial value of $\theta_i$, said new values of $\theta_p$ and $\phi_p$ defining the location of a potential refraction point corresponding to said one element;

c) means for determining if said calculated new values for $\theta_p$ and $\phi_p$ define a point on the surface of the spherical work piece such that a wave emitted from said one element passes through the pre-selected focal point; and d) if said calculated new values for $\theta_p$ and $\phi_p$ do not define a point on the surface of the spherical work piece such that a wave emitted from said one element passes through the pre-selected focal point, then calculating a new initial value for $\theta_{(i+1)}$ as a function of a pre-selected incremental factor and the value $\theta_i$ then incrementing (i) and repeating substeps (b) through (d) with the new value $\theta_i$.

14. The apparatus of claim 13, wherein the means for calculating new values for $\theta_p$ and $\phi_p$ includes a means responsive to a function of angles $\phi_e$, $\theta_e$, $\phi_f$, $\theta_f$, said angles $\phi_e$, $\theta_e$ defining the location of said one element of said phased array relative to the center of the spherical work piece, and said angles $\phi_f$, $\theta_f$ defining the location of the focal point relative to the center of the spherical work piece.

15. The apparatus of claim 14, wherein the means for calculating new values for $\theta_p$ and $\phi_p$ is further responsive to a function of angles $\beta$ and $\beta_f$, said angle $\beta$ constituting an angle formed by a line extending between the center of the spherical work piece and said one element of the phased array mechanism and a line extending between the center of the spherical work piece and said potential refraction point.

16. The apparatus of claim 15, further including a means for calculating wherein angle $\beta$ is calculated according to the formula, $\beta=\theta_i-\sin^{-1}[(R_0/R_e)\sin(\theta_i)]$, where $R_0$ is the radius of the spherical work piece and $R_e$ is the distance between the center of the spherical work piece and said element of the phased array.

17. The apparatus of claim 15, wherein the means for calculating new values for $\theta_p$ and $\phi_p$ comprises means for performing the following steps:

(i) determining if $\phi_e=0$ and $\phi_f=0$, and, if so, assigning $\phi_p=0$ and assigning $\theta_p$ equal to any arbitrary value;

(ii) determining if $\phi_e=0$ and $\phi_f\neq 0$ and $\phi_f\neq 180°$, and, if so, then assigning $\phi_p=\beta$ and assigning $\theta_p=\theta_f$;

(iii) determining if $\phi_e\neq 0$ and $\phi_f=0$ and $\phi_e\neq 180°$, and, if so, then assigning $\phi_p=\beta_f$ and assigning $\theta_p=\theta_e$;

(iv) determining if $\phi_e=180°$ and $\phi_f=180°$, and, if so, assigning $\phi_p=180°$ and assigning $\theta_p$ to any arbitrary value;

(v) determining if $\phi_e=180°$ and $\phi_f\neq 180°$ and $\phi_f\neq 0°$, and, if so, assigning $\phi_p=180°-\beta$ and assigning $\theta_p=\theta_f$;

(vi) determining if $\phi_f=180°$ and $\phi_e\neq 180°$ and $\phi_e\neq 0°$, and, if so, assigning $\phi_p=180°-\beta_f$ and assigning $\theta_p=\theta_e$;

(vii) determining if $\phi_e=90°$ and $\phi_f=90°$ and $\theta_f>\theta_e$, and, if so, assigning $\phi_p=90°$ and assigning $\theta_p=\beta+\theta_e$;

(viii) determining if $\phi_e=90°$ and $\phi_f=90°$ and $\theta_f<\theta_e$, and, if so, assigning $\phi_p=90°$ and assigning $\theta_p=\theta_e-\beta$;

(ix) determining if $\theta_e=\theta_f$ and $\phi_e=\phi_f$ and $\phi_f\neq 0$, and, if so, assigning $\phi_p=\phi_e$ and assigning $\theta_p=\theta_e$;

(x) determining if $\theta_e=\theta_f$ and $\phi_e\neq\phi_f$ and $\phi_p\neq 0$, and, if so, assigning $\theta_p=\theta_e$ and assigning $\phi_p=180°-\cos^{-1}[\{\cos(\beta)\sin(\phi_f)-\cos(\beta_f)\sin(\phi_e)\}/\{\sin(\phi_e-\phi_f)\}]$;

if none of the conditions in steps (i) through (x) are satisfied, then assigning values to $\theta_p$ and $\phi_p$ as a function of $\phi_e$, $\theta_e$, $\phi_f$, $\theta_f$.

18. The apparatus of claim 17, wherein the means for assigning values to $\theta_p$ and $\phi_p$ as a function of $\phi_e$, $\theta_e$, $\phi_f$, $\theta_f$ comprises means for performing the following steps:

assigning $\phi_p=\cos^{-1}[-B/A]$ where, $B=\cos(\beta)\sin(\phi_f)[\sin(\phi_e)\cos(\phi_f)\cos(\theta_f-\theta_e)-\cos(\phi_e)\sin(\phi_f)]$ $+\cos(\beta_f)\sin(\phi_e)[\sin(\phi_f)\cos(\phi_e)\cos(\theta_f-\theta_e)-\cos(\phi_f)\sin(\phi_e)]$ and, $A=\cos(\phi_f)\sin(\phi_e)[\sin(\phi_e)\cos(\phi_f)-\cos(\phi_e)\sin(\phi_f)\cos(\theta_f-\theta_e)]$ $+\cos(\phi_e)\sin(\phi_f)[\sin(\phi_f)\cos(\phi_e)-\cos(\phi_f)\sin(\phi_e)\cos(\theta_f-\theta_e)]+\sin^2(\phi_e)\sin^2(\phi_f)\sin^2(\theta_f-\theta_e);$ and assigning $\theta_p=\sin^{-1}\{[\cos(\beta)\sin(\phi_f)\cos(\theta_f)-\cos(\beta_f)\sin(\phi_e)\cos(\theta_e)-(\sin(\phi_f)\cos(\theta_f)\cos(\theta_e)-\sin(\phi_e)\cos(\theta_e)\cos(\phi_f))\cos(\phi_p)]/(\sin(\phi_p)\sin(\phi_f)\sin(\phi_e)\sin(\theta_e-\theta_f))\}$.

19. The apparatus of claim 18, wherein the step of calculating new values for $\theta_p$ and $\phi_p$ further comprises the step of adjusting the value of $\theta_p$ according to the following conditions:

If $\sin(\theta_p)>0$ and $\cos(\theta_p)>0$, then $\theta_p=\theta_p$;
If $\sin(\theta_p)>0$ and $\cos(\theta_p)<0$, then $\theta_p=180-\theta_p$;
If $\sin(\theta_p)<0$ and $\cos(\theta_p)<0$, then $\theta_p=180-\theta_p$; and
If $\sin(\theta_p)<0$ and $\cos(\theta_p)>0$, then $\theta_p=360+\theta_p$.

20. The apparatus of claim 13, wherein the means for calculating said pulse firing time for each element of the phased array mechanism comprises a means for performing the substeps of:

calculating an element delay value for each element of the phased array mechanism;

determining the minimum value of all of said element delay values;

subtracting said minimum value from each of said element delay values.

21. An apparatus for focusing ultrasonic waves emitted from a plurality of elements of a phased array mechanism and directed toward a spherical nuclear reactor pressure vessel head, having a surface and a center, to arrive at a pre-selected focal point at the same time and in phase, comprising:

means for calculating the location of at least one of a plurality of preferred refraction points on a surface of the spherical vessel head using an iterative process, each of said preferred refraction points corresponding to one of the elements of the phased array mechanism and each of said preferred refraction points being uniquely defined relative to the location of the center of the spherical vessel head by a first angle, $\theta_p$, representing a rotation about a first spatial axis, and a second angle, $\phi_p$, representing a rotation about a second spatial axis; and means for calculating a pulse firing time for each element of the phased array mechanism that relates to the relative timing of the emitted waves from the elements.

22. The apparatus of claim 21, wherein the means for calculating the location of at least one of the preferred refraction points comprises means for performing the substeps of: a) choosing an initial value for $\theta_i$ corresponding to one element of the phased array mechanism where (i) represents the number of times that the iterative process has been repeated and $\theta_0$ represents a preselected initial angle, for the beginning of the iterative process;

b) calculating new values for $\theta_p$ and $\phi_p$ based upon said initial value of $\theta_i$, said new values of $\theta_p$ and $\phi_p$ defining the location of a potential refraction point corresponding to said one element;

c) determining if said calculated new values for $\theta_p$ and $\phi_p$ define a point on the surface of the spherical work piece such that a wave emitted from said one element passes through the pre-selected focal point; and d) if said calculated new values for $\theta_p$ and $\phi_p$ do not define a point on the surface of the spherical work piece such that a wave emitted from said one element passes through the pre-selected focal point, then calculating a new initial value for $\theta_{(i+1)}$ as a function of a preselected incremental factor and the value $\theta_i$ then incrementing (i) and repeating substeps (b) through (d) with the new value $\theta_i$.

\* \* \* \* \*